United States Patent
Swoyer et al.

(10) Patent No.: US 8,886,303 B1
(45) Date of Patent: *Nov. 11, 2014

(54) PRE-SUTURED ANCHOR FOR IMPLANTABLE LEADS

(71) Applicant: Greatbatch, Ltd., Clarence, NY (US)

(72) Inventors: John Swoyer, Andover, MN (US); Jesse Geroy, Ham Lake, MN (US); James Finley, Minneapolis, MN (US)

(73) Assignee: Greatbatch, Ltd., Clarence, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/857,214

(22) Filed: Apr. 5, 2013

Related U.S. Application Data

(63) Continuation of application No. 13/046,182, filed on Mar. 11, 2011, now Pat. No. 8,437,846.

(51) Int. Cl.
*A61N 1/05* (2006.01)
*A61B 17/04* (2006.01)

(52) U.S. Cl.
CPC .......... *A61N 1/0558* (2013.01); *A61B 17/0401* (2013.01)
USPC ............... 607/2; 607/126; 607/132; 606/148; 606/228; 606/232

(58) Field of Classification Search
CPC .............................................. A61B 2017/0477
See application file for complete search history.

(56) References Cited

U.S. PATENT DOCUMENTS

| | | |
|---|---|---|
| 3,241,554 A | 3/1966 | Coanda |
| 4,516,584 A | 5/1985 | Garcia |
| 4,553,961 A | 11/1985 | Pohndorf et al. |
| 4,672,979 A | 6/1987 | Pohndorf |
| 4,683,895 A | 8/1987 | Pohndorf |
| 4,744,370 A | 5/1988 | Harris |
| 5,178,629 A | 1/1993 | Kammerer |
| 5,273,053 A | 12/1993 | Pohndorf |
| 5,476,493 A | 12/1995 | Muff |
| 5,484,445 A | 1/1996 | Knuth |
| 5,584,874 A | 12/1996 | Rugland et al. |
| 5,690,676 A | 11/1997 | Dipoto et al. |
| 5,716,368 A | 2/1998 | de la Torre et al. |
| 5,843,146 A | 12/1998 | Cross, Jr. |
| 5,957,968 A | 9/1999 | Belden et al. |
| 6,134,477 A | 10/2000 | Knuteson |
| 6,685,728 B2 | 2/2004 | Sinnott et al. |
| 6,932,834 B2 | 8/2005 | Lizardi et al. |
| 7,082,337 B2 | 7/2006 | Sommer et al. |
| 7,390,329 B2 | 6/2008 | Westra et al. |
| 7,824,421 B2 | 11/2010 | Weisenburgh et al. |
| 8,249,719 B2 | 8/2012 | Bodner et al. |
| 8,249,720 B2 | 8/2012 | Verzal et al. |

(Continued)

*Primary Examiner* — Kennedy Schaetzle
(74) *Attorney, Agent, or Firm* — Michael P. Horvath

(57) ABSTRACT

A pre-sutured anchor including a deformable anchor sleeve with a lumen sized to receive the therapy delivery element. An outer surface of the anchor sleeve including one or more annular compression grooves oriented generally co-axial to the lumen. At least one compression member is located in a compression groove in an open configuration. The compression member includes at least one stop. A suture material pre-tied in a self-locking compression knot extends around each compression member. The suture material includes distal ends adapted to receive a tension force that is transmitted as a radial compression force to deform the compression members and substantially engage the stop in a compressed configuration. The anchor sleeve compressively engages the therapy delivery element in the compressed configuration.

20 Claims, 12 Drawing Sheets

(56) References Cited

U.S. PATENT DOCUMENTS

| | | |
|---|---|---|
| 8,271,096 B2 | 9/2012 | Rivard et al. |
| 8,437,846 B2 * | 5/2013 | Swoyer et al. .................. 607/2 |
| 2008/0243151 A1 | 10/2008 | Binmoeller et al. |
| 2008/0312664 A1 | 12/2008 | Bardsley et al. |
| 2009/0125060 A1 | 5/2009 | Rivard et al. |
| 2010/0049277 A1 | 2/2010 | Wahlstrand et al. |
| 2010/0174240 A1 | 7/2010 | Wells et al. |
| 2010/0198258 A1 | 8/2010 | Heaven et al. |
| 2012/0232627 A1 | 9/2012 | Swoyer et al. |

* cited by examiner

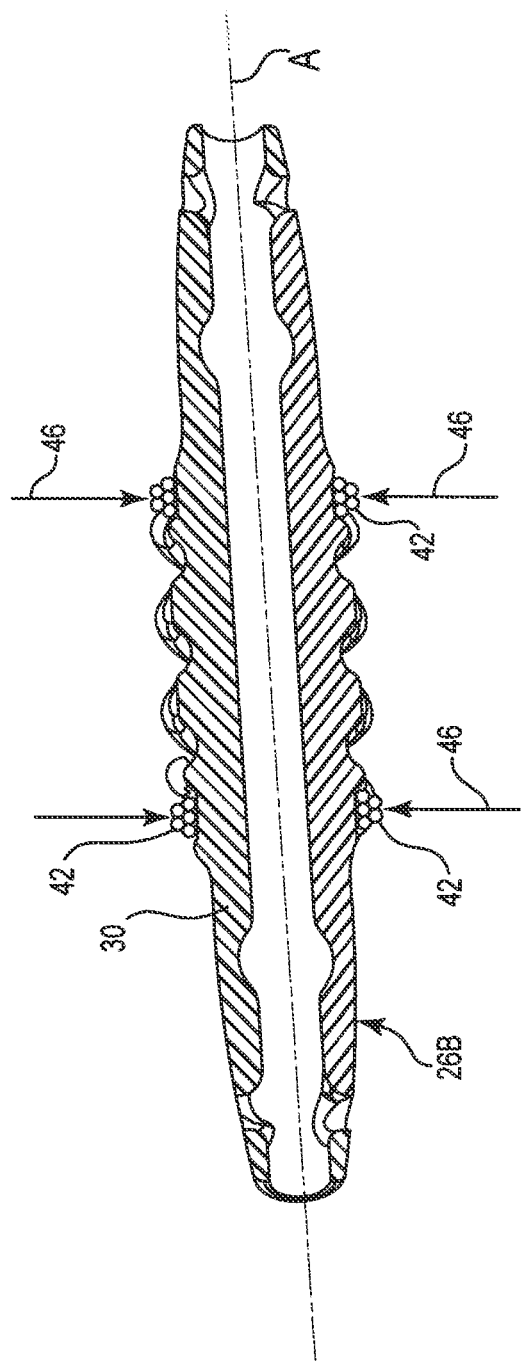

PRE-SUTURED ANCHOR FOR IMPLANTABLE LEADS

CLAIM OF PRIORITY

This application is a continuation of and claims the benefit of priority under 35 U.S.C. §120 to Swoyer et al., U.S. patent application Ser. No. 13/046,182, now U.S. Pat. No. 8,437,846, entitled "PRE-SUTURED ANCHOR FOR IMPLANTABLE LEADS", filed on Mar. 11, 2011, which is incorporated by reference herein in its entirety.

FIELD

The present disclosure relates to pre-sutured anchors for securing therapy delivery elements, such as stimulation leads or catheters, within a living body. A suture material configured as a self-locking knot is wrapped around compression members engaged with the anchor. Tensioning the ends of the suture material deforms the compression members and compressively engages the anchor to the therapy delivery element.

BACKGROUND

Implantable medical devices are used for a wide variety of medical conditions, such as for example, cardiac pace making, cardiac rhythm management, treatments for congestive heart failure, implanted defibrillators, and neurostimulation. Neurostimulation encompasses a wide range of applications, such as for example, pain control, nervous tremor mitigation, incontinent treatment, epilepsy seizure reduction, and vagus nerve stimulation for clinical depression.

These implantable medical devices generally include an implanted pulse generator that generates electrical pulses or signals that are transmitted to a targeted tissue or nerves through a therapy delivery element, such as a lead with electrodes. Controlled placement of the therapy delivery element is required for improved therapeutic efficacy or reduced side effects. Retaining the implanted therapy delivery element in the desired location also creates difficulties because the location may change over time as the patient moves. A variety of anchors are available to prevent the therapy delivery element from migrating away from a specifically selected stimulation site.

U.S. Pat. No. 4,553,961 (Pohndorf et al.) discloses a typical suture sleeve with an outer elastomeric sleeve and an inner gripping structure. The lead is inserted though a lumen in the anchor. The gripping structure is radially compressed by the surgeon tying a suture material around the suture sleeve. The suture material causes the outer elastomeric sleeve to compress the inner gripping structure, which then collapses onto and grips the lead.

Clinicians inserting and anchoring therapy delivery elements typically prefer to perform the procedure rapidly, in a minimally invasive manner, and fix the therapy delivery element in a manner that reduces the opportunity for the therapy delivery element to migrate if practicable. Examples of some previous anchors are shown in U.S. Pat. No. 6,134,477 "Adjustable Medical Lead Fixation System" by Knuteson (Oct. 17, 2000); U.S. Pat. No. 5,484,445 "Sacral Lead Anchoring System" by Knuth (Jan. 16, 1996); and, U.S. Pat. No. 5,843,146. "Adjustable Medical Lead Anchor" by Cross, Jr. (Dec. 1, 1998).

These prior anchors require the surgeon to wrap the suture material around the anchor, and/or tie the knot. This approach is difficult to perform using minimally invasive techniques, and introduces variation in the procedure because of differing suturing skills between surgeons and the suture material selected for this application.

BRIEF SUMMARY

The present disclosure relates to pre-sutured anchors for securing therapy delivery elements, such as stimulation leads or catheters, within a living body. A suture material configured as a self-locking knot is wrapped around the anchor. Tensioning the ends of the suture material deforms the anchor and compressively engages the anchor to the therapy delivery element.

The present pre-sutured anchor works by using pre-tied knots to constrict a silicone sleeve onto the lead. As the sleeve compresses down, it builds a mechanical resistance lock that prevents the lead from moving through the pre-sutured anchor. To ensure that the pre-sutured anchor does not constrict too far and possibly damage the lead, compression members are optionally added beneath the pre-tied sutures. The compression members move inward as the pre-tied knots are tightened, but only until edges of the compression members abut against one another. At that point the compression members can no longer move regardless of how hard the sutures are tightened. Thus, the compression members help maintain an optimum amount of compression without damaging the therapy delivery element.

In one embodiment, the anchor includes a deformable anchor sleeve with a lumen sized to receive the therapy delivery element, and an outer surface with one or more annular compression grooves oriented generally co-axial to the lumen. At least one compression member is located in a compression groove in an open configuration. The compression member includes at least one stop. A suture material pre-tied in a self-locking compression knot extends around each compression member. The suture material includes distal ends adapted to receive a tension force that is transmitted as a radial compression force to deform the compression members and substantially engage the stop in a compressed configuration. The anchor sleeve compressively engages the therapy delivery element in the compressed configuration.

The compression member can be a variety of one-piece or multi-piece structures and can have one or more stops. The compression members are preferably oriented concentrically around the therapy delivery element in the compressed configuration.

Edges of the compression member engage in the compressed configuration to limit application of the radial compression force on the anchor sleeve and the therapy delivery element. The compression members preferably plastically deforms in response to the radially inward force. The compression member can be one of a thermoplastic material, stainless steel, or Nitinol. The self-locking compression knot is preferably a nail knot. The self-locking compression knot preferably includes at least three loops around the compression member to better distribute the radially compressive force. In one embodiment, the anchor sleeve includes at least one fill port adapted to receive a medical adhesive.

The present disclosure is also directed to a neurostimulation system that includes an implantable pulse generator and a therapy delivery element. A proximal end of the therapy delivery element is adapted to electrically couple with the implantable pulse generator and a distal end with a plurality of electrodes electrically coupled to the implantable pulse generator. An anchor as disclosed herein is provided for securing the therapy delivery element in a desired location within a living body.

The present disclosure is also directed to a method of securing a therapy delivery element at a desired location within a living body. The method includes the steps of inserting the therapy delivery element through a lumen of an anchor of the present disclosure. The anchor is slid along the therapy delivery element to the desired location. The anchor is attached to the desired location within the living body. A tension force is applied to distal ends of the self-locking compression knot that is transmitted as a radial compression force to deform the compression members and substantially close a gap in the compression members in a compressed configuration. The anchor sleeve compressively engages the anchor sleeve in the compressed configuration.

The method preferably includes engaging edges of the compression member at the stop in the compressed configuration to limit application of the radial compression force on the anchor sleeve and the therapy delivery element. The compression member is preferably plastically deformed in response to the radially inward force. The compression member is preferably generally concentric with the therapy delivery element in the compressed configuration.

The present disclosure is also directed to a method of implanting a neurostimulation system within a living body. An implantable pulse generator is implanted within the living body. Electrodes at a distal end of a therapy delivery element are located at a target location within the living body. A proximal end of the therapy delivery element is inserted through a lumen of an anchor of the present disclosure. The anchor is slid along the therapy delivery element to the desired location. The anchor is attached to the desired location within the living body. A tension force is applied to distal ends of the self-locking compression knot that is transmitted as a radial compression force to deform the compression members and substantially engage a stop in a compressed configuration. The anchor sleeve compressively engages the anchor sleeve in the compressed configuration. Proximal ends of the therapy delivery element are electrically coupled to the implantable pulse generator.

BRIEF DESCRIPTION OF THE SEVERAL VIEWS OF THE DRAWING

FIG. 10 is a variation of the pre-sutured anchor of FIG. 2, without the compression members, in accordance with an embodiment of the present disclosure.

DETAILED DESCRIPTION OF SOME EMBODIMENTS

The description that follows relates to a spinal cord stimulation (SCS) system. However, it is to be understood that the while the present disclosure lends itself well to applications in SCS, the disclosure in its broadest aspects may not be so limited. Rather, the disclosure may be used with any type of implantable therapy delivery system with one or more therapy delivery elements. For example, the present disclosure may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

In another embodiment, one or more of the therapy delivery elements may be a fluid delivery conduit, such as a catheter, including an inner lumen that is placed to deliver a fluid, such as pharmaceutical agents, insulin, pain relieving agents, gene therapy agents, or the like from a fluid delivery device (e.g., a fluid reservoir and/or pump) to a respective target tissue site in a patient.

In yet another embodiment, one or more of the therapy delivery elements may be an electrical lead including one or more sensing electrodes to sense physiological parameters (e.g., blood pressure, temperature, cardiac activity, etc.) at a target tissue site within a patient. In the various embodiments contemplated by this disclosure, therapy may include stimulation therapy, sensing or monitoring of one or more physiological parameters, fluid delivery, and the like. "Therapy delivery element" includes pacing or defibrillation leads, stimulation leads, sensing leads, fluid delivery conduit, extensions for any of the above, or combinations thereof. "Target tissue site" refers generally to the target site for implantation of a therapy delivery element, regardless of the type of therapy.

Figure 1A:
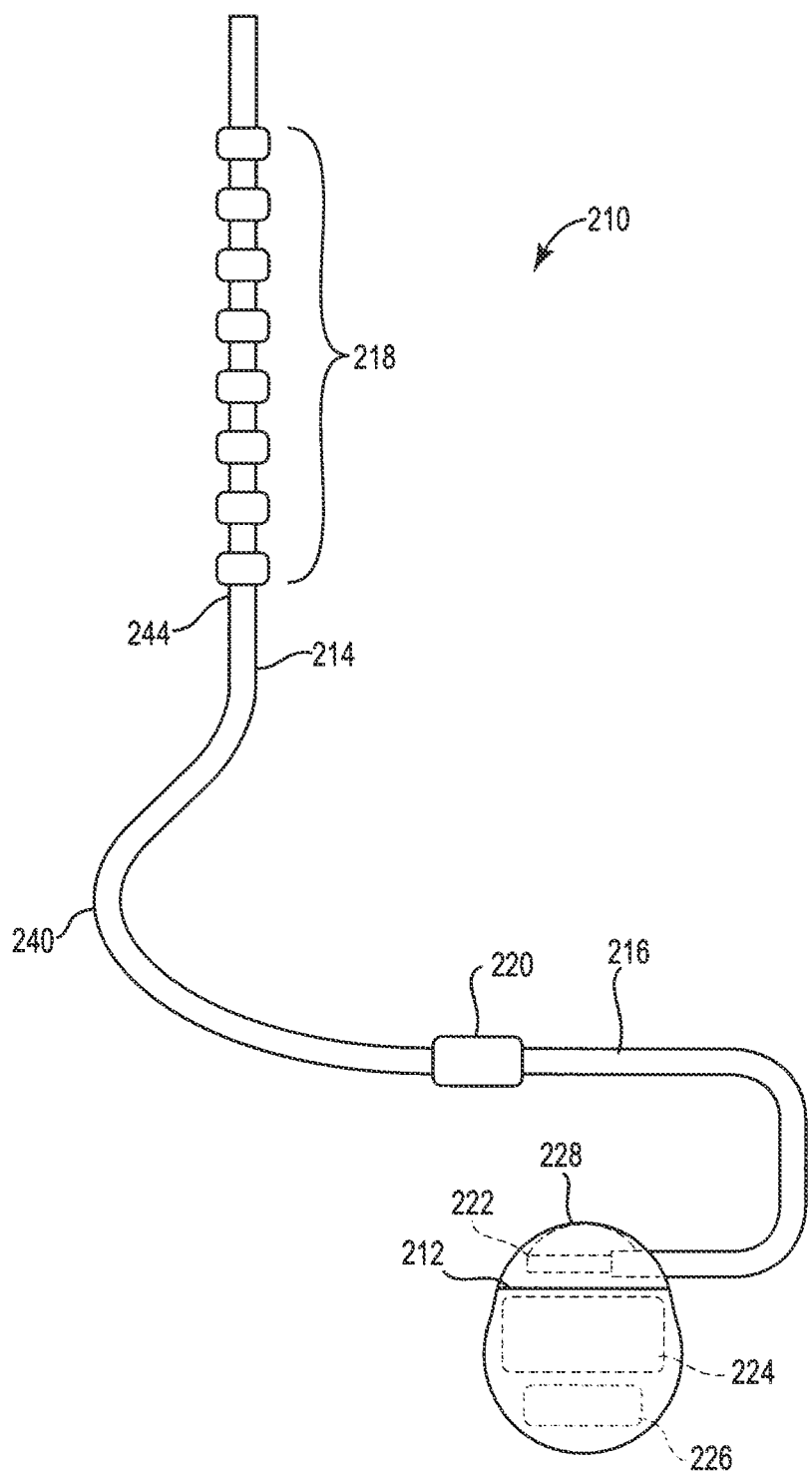
FIG. 1A is a schematic illustration of a therapy delivery system.

FIG. 1A illustrates a generalized therapy delivery system 210 that may be used in spinal cord stimulation (SCS), as well as other stimulation applications. The therapy delivery system 210 generally includes an implantable pulse generator 212, an implantable therapy delivery element 214, which carries an array of electrodes 218 (shown exaggerated for purposes of illustration), and an optional implantable extension lead 216. Although only one therapy delivery element 214 is shown, typically two or more therapy delivery elements 214 are used with the therapy delivery system 210 (See e.g., FIG. 1C).

The therapy delivery element 214 includes elongated body 240 having a proximal end 236 and a distal end 244. The elongated body 240 typically has a diameter of between about 0.03 inches to 0.07 inches and a length within the range of 30 cm to 90 cm for spinal cord stimulation applications. The elongated body 240 may be composed of a suitable electrically insulative material, such as, a polymer (e.g., polyurethane or silicone), and may be extruded from as a uni-body construction.

In the illustrated embodiment, proximal end 236 of the therapy delivery element 214 is electrically coupled to distal end 238 of the extension lead 216 via a connector 220, typically associated with the extension lead 216. Proximal end 242 of the extension lead 216 is electrically coupled to the implantable pulse generator 212 via connector assembly 222 associated with housing 228. Alternatively, the proximal end 236 of the therapy delivery element 214 can be electrically coupled directly to the connector 220.

In the illustrated embodiment, the implantable pulse generator 212 includes electronic subassembly 224 (shown schematically), which includes control and pulse generation circuitry (not shown) for delivering electrical stimulation energy to the electrodes 218 of the therapy delivery element 214 in a controlled manner, and a power supply, such as battery 226.

The implantable pulse generator 212 provides a programmable stimulation signal (e.g., in the form of electrical pulses or substantially continuous-time signals) that is delivered to target stimulation sites by electrodes 218. In applications with more than one therapy delivery element 214, the implantable pulse generator 212 may provide the same or a different signal to the electrodes 218.

Alternatively, the implantable pulse generator 212 can take the form of an implantable receiver-stimulator in which the power source for powering the implanted receiver, as well as control circuitry to command the receiver-stimulator, are contained in an external controller inductively coupled to the receiver-stimulator via an electromagnetic link. In another embodiment, the implantable pulse generator 212 can take the form of an external trial stimulator (ETS), which has similar pulse generation circuitry as an IPG, but differs in that it is a non-implantable device that is used on a trial basis after the therapy delivery element 214 has been implanted and prior to implantation of the IPG, to test the responsiveness of the stimulation that is to be provided.

The housing 228 is composed of a biocompatible material, such as for example titanium, and forms a hermetically sealed compartment containing the electronic subassembly 224 and battery 226 is protected from the body tissue and fluids. The connector assembly 222 is disposed in a portion of the housing 228 that is, at least initially, not sealed. The connector assembly 222 carries a plurality of contacts that electrically couple with respective terminals at proximal ends of the therapy delivery element 214 or extension lead 216. Electrical conductors extend from the connector assembly 222 and connect to the electronic subassembly 224.

Figure 1B:
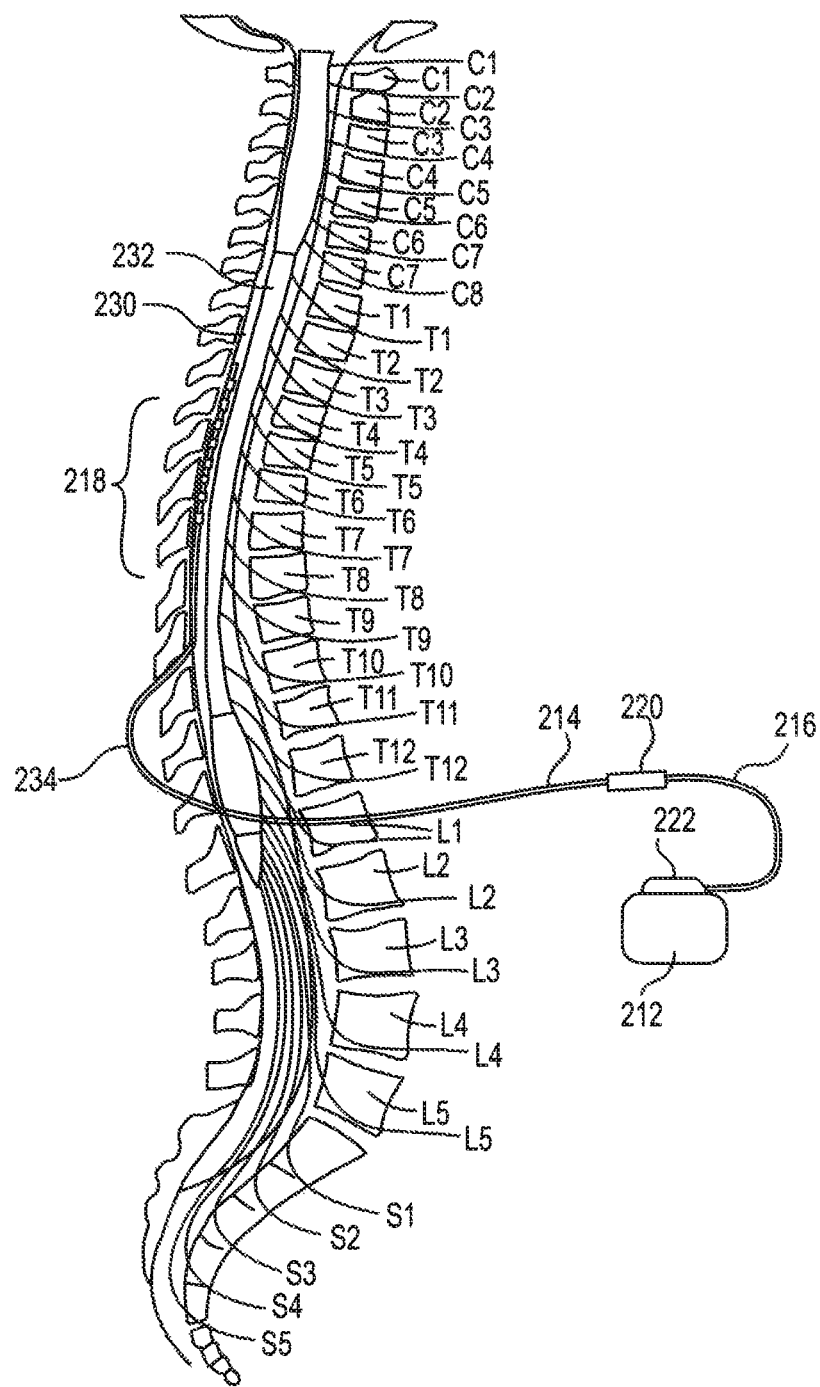
FIG. 1B is a schematic illustration of an environment for a therapy delivery system in accordance with an embodiment of the present disclosure.

FIG. 1B illustrates the therapy delivery element 214 implanted in the epidural space 230 of a patient in close proximity to the dura, the outer layer that surrounds the spinal cord 232, to deliver the intended therapeutic effects of spinal cord electrical stimulation. The target stimulation sites may be anywhere along the spinal cord 232, such as for example proximate the sacral nerves.

Figure 1C:
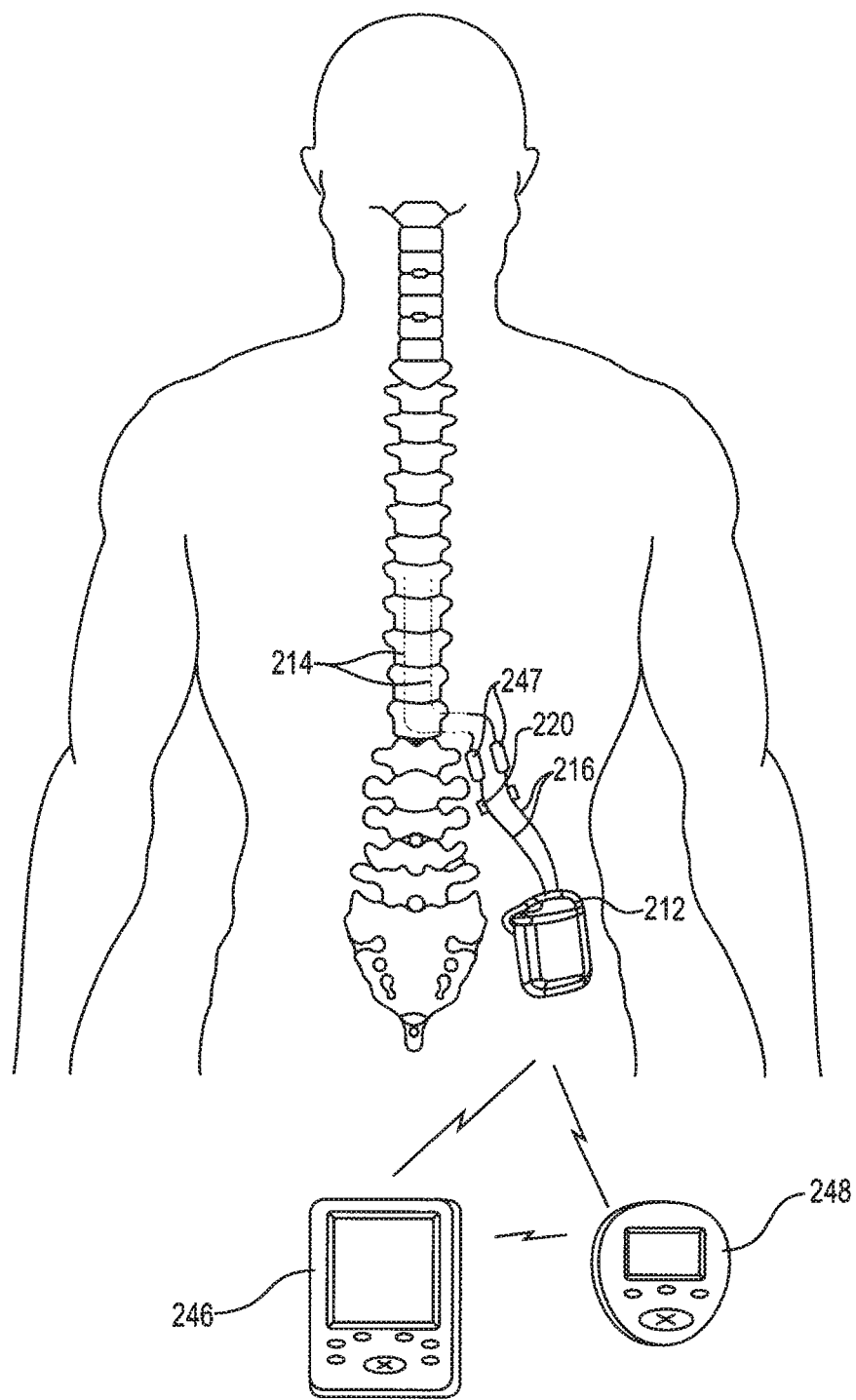
FIG. 1C is an alternate illustration of the environment for an implantable pulse generator with a therapy delivery element in accordance with an embodiment of the present disclosure.

Because of the lack of space near the lead exit point 234 where the therapy delivery element 214 exits the spinal column, the implantable pulse generator 212 is generally implanted in a surgically-made pocket either in the abdomen or above the buttocks, such as illustrated in FIG. 1C. The implantable pulse generator 212 may, of course, also be implanted in other locations of the patient's body. Use of the extension lead 216 facilitates locating the implantable pulse generator 212 away from the lead exit point 234. In some embodiments, the extension lead 216 serves as a lead adapter if the proximal end 236 of the therapy delivery element 214 is not compatible with the connector assembly 222 of the implantable pulse generator 212, since different manufacturers use different connectors at the ends of their stimulation leads and are not always compatible with the connector assembly 222.

As illustrated in FIG. 1C, the therapy delivery system 210 also may include a clinician programmer 246 and a patient programmer 248. Clinician programmer 246 may be a handheld computing device that permits a clinician to program neurostimulation therapy for patient using input keys and a display. For example, using clinician programmer 246, the clinician may specify neurostimulation parameters for use in delivery of neurostimulation therapy. Clinician programmer 246 supports telemetry (e.g., radio frequency telemetry) with the implantable pulse generator 212 to download neurostimulation parameters and, optionally, upload operational or physiological data stored by implantable pulse generator 212. In this manner, the clinician may periodically interrogate the implantable pulse generator 212 to evaluate efficacy and, if necessary, modify the stimulation parameters.

Similar to clinician programmer 246, patient programmer 248 may be a handheld computing device. Patient programmer 248 may also include a display and input keys to allow patient to interact with patient programmer 248 and the implantable pulse generator 212. The patient programmer 248 provides patient with an interface for control of neurostimulation therapy provided by the implantable pulse generator 212. For example, patient may use patient programmer 248 to start, stop or adjust neurostimulation therapy. In particular, patient programmer 248 may permit patient to adjust stimulation parameters such as duration, amplitude, pulse width and pulse rate, within an adjustment range specified by the clinician via clinician programmer 248, or select from a library of stored stimulation therapy programs.

The implantable pulse generator 212, clinician programmer 246, and patient programmer 248 may communicate via cables or a wireless communication. Clinician programmer 246 and patient programmer 248 may, for example, communicate via wireless communication with the implantable pulse generator 212 using RF telemetry techniques known in the art. Clinician programmer 246 and patient programmer 248 also may communicate with each other using any of a variety of local wireless communication techniques, such as RF communication according to the 802.11 or Bluetooth specification sets, infrared communication, e.g., according to the IrDA standard, or other standard or proprietary telemetry protocols.

Since the implantable pulse generator 212 is located remotely from target location 249 for therapy, the therapy delivery element 214 and/or the extension leads 216 is typically routed through a pathways subcutaneously formed along the torso of the patient to a subcutaneous pocket where the implantable pulse generator 212 is located. As used hereinafter, "lead" and "lead extension" are used interchangeably, unless content clearly dictates otherwise.

The therapy delivery elements 214 are typically fixed in place near the location selected by the clinician using the present pre-sutured anchor 247, such as in the epidural space 230. The pre-sutured anchor 247 can be positioned on the therapy delivery element 214 in a wide variety of locations and orientations to accommodate individual anatomical differences and the preferences of the clinician. The pre-sutured anchor 247 may then be affixed to tissue using fasteners, such as for example, one or more sutures, staples, screws, or other fixation devices. The tissue to which the pre-sutured anchor 247 is affixed may include subcutaneous fascia layer, bone, or some other type of tissue. Securing the pre-sutured anchor 247 to tissue in this manner prevents or reduces the chance that the therapy delivery element 214 will become dislodged or will migrate in an undesired manner.

Figure 2:
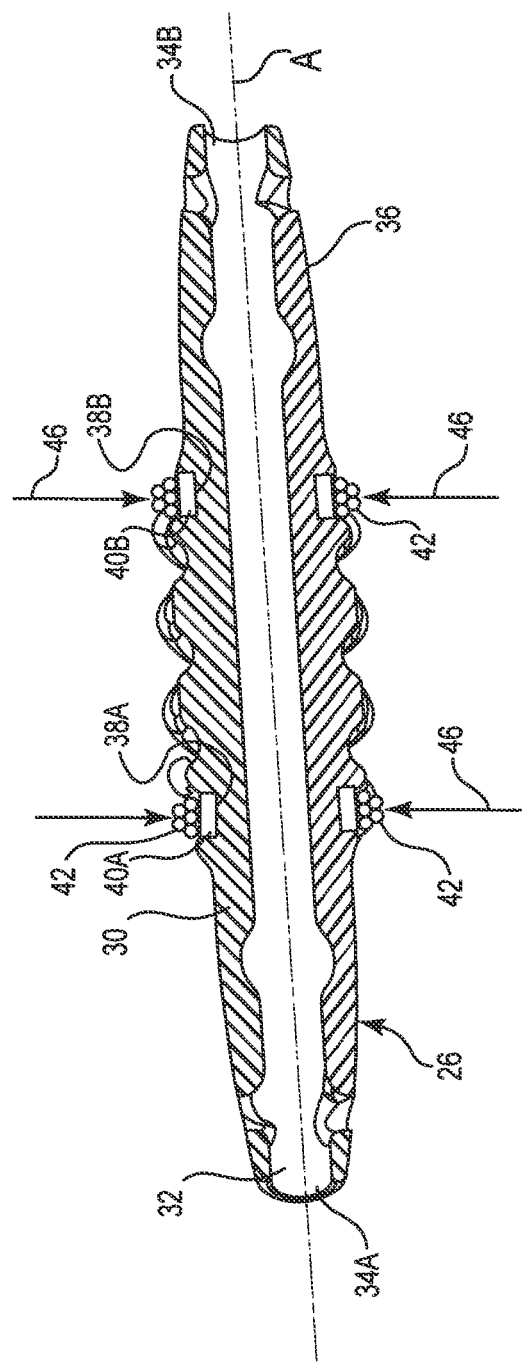
FIG. 2 is a sectional view of a pre-sutured anchor for a therapy delivery element with a pre-tied knot in accordance with an embodiment of the present disclosure.
Figure 3:
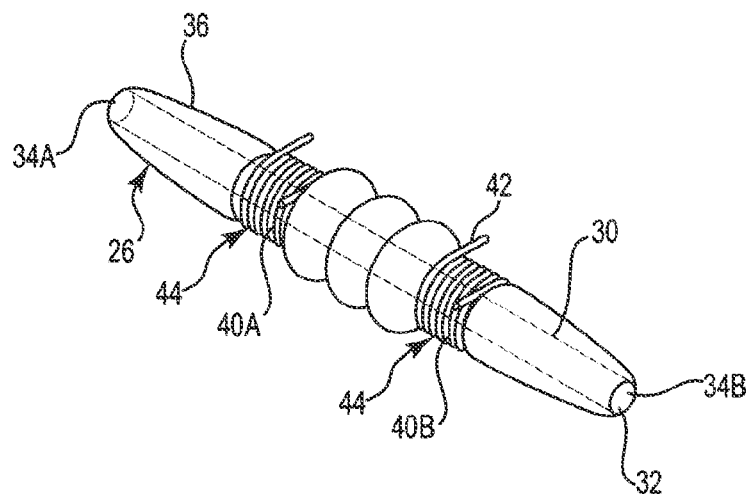
FIG. 3 is a perspective view of the pre-sutured anchor of FIG. 2.

FIGS. 2 and 3 illustrate pre-sutured anchor 26 in accordance with an embodiment of the present disclosure. Anchor sleeve 30 includes primary lumen 32 extending along axis A from first opening 34A to second opening 34B ("34"). The primary lumen 32 preferably has a larger diameter than outside diameter of therapy delivery element 24 (see FIG. 4A) to permit easy positioning of the pre-sutured anchor 26. The anchor sleeve 32 is preferably constructed from an elastomeric material, such as for example, medical grade silicone.

Outer surface 36 of the anchor sleeve 30 includes one or more compression grooves 38A, 38B ("38") containing one or more compression members 40A, 40B ("40"). The compression members 40 can be a one-piece structure, such as for example a C-shaped band illustrated in FIGS. 9A and 9B, or a variety of multi-piece structure (see e.g., FIGS. 4A and 4B).

Suture material 42 is wrapped around the compression members 40. The compression members 40 are preferably recessed in the compression grooves 38 to retain the suture material 42 in the desired axial location along axis A. The compression members 40 are optionally attached to the anchor sleeve 30, such as for example, using medical adhesive, liner, mechanical interlocks and the like.

The compression members 40 can be any rigid or semi-rigid material, such as for example, a thermoplastic or thermoset material, stainless steel, Nitinol, or a combination thereof. In another embodiment, the compression members 40 are radiopaque to facilitate medical imaging.

The suture material 42 is preferably configured as a pre-tied, self-locking compression knot 44, such as for example, a nail knot. Using a nail knot spreads the radial compression force 46 over a larger surface of the anchor sleeve 30, increasing frictional engagement with the therapy delivery element 24 and reducing the risk of damage to the pre-sutured anchor 26. The pre-tied knot 44 removes variation out of the process by requiring all surgeons to use the same suture material 42 and the same pre-tied knot 44. As used herein, "compression knot" refers to one or more loops of suture material that contracts when one or more distal ends of the suture material are tensioned. "Self-locking" refers to a knot that relies on friction between the suture material to substantially maintain a radially compressive force on a structure.

Figure 4A:
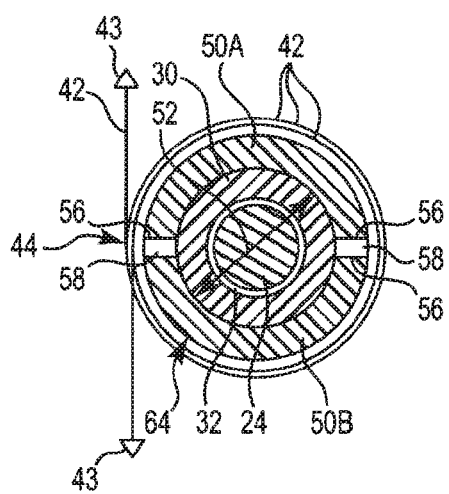
FIG. 4A is a sectional view of the pre-sutured anchor of FIG. 2 before the pre-tied knot is tensioned.

As best illustrated in FIG. 4A, the compression members 40 include an upper portion 50A and a lower portion 50B ("50") shown in an open configuration 64. The compression members 40 have an inside diameter 52 in the open configuration 64 about the same as outside diameter 52 of the compression grooves 38 on the anchor sleeve 30 so as to avoid constriction of the lumen 32.

The compression members 40 are preferably discontinuous. For example, in the illustrated embodiment, the compression members 40 include compression gaps 58 between stops 56 of the upper and lower portions 50. In the illustrated embodiment, the upper and lower portions 50 are two individual steel arches that are attached to the anchor sleeve 30 with medical adhesive and a thin liner.

In one embodiment, break-away tabs 43 are attached to distal ends 62 of the suture material 42. The break-away tabs 43 are designed to apply a tension force 60 sufficient to close the gaps 58, without over tightening. The break-away tabs 43 preferably disconnect from the suture material 42 after the gap 58 is closed.

Figure 4B:
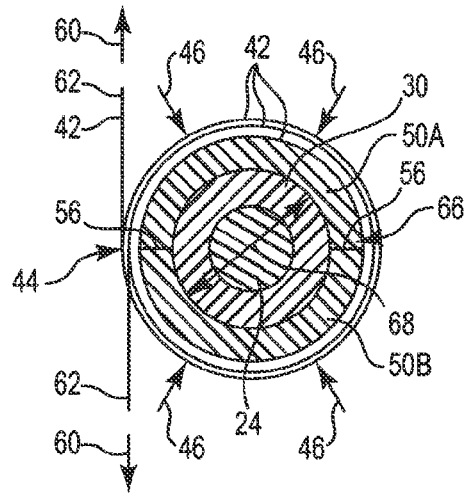
FIG. 4B is a sectional view of the pre-sutured anchor of FIG. 2 after the pre-tied knot is tensioned.

As best illustrated in FIG. 4B, tension force 60 is applied to distal ends 62 of the suture material 42, which generates radial compression force 46 that is applied to the compression members 40. The upper and lower portions 50 of the compression members 40 are displaced radially inward by the force 46 until stops 56 engage in compressed configuration 66. The discontinuous nature of the compression members 40 permits the compression gaps 58 to be closed to form the compressed configuration 66.

The compression members 40 preferably an inside diameter 68 in the compressed configuration 66 that is less than outside diameter 52 of the anchor sleeve 30. The force 46 is sufficient to elastically deform the anchor sleeve 30 a sufficient amount to frictionally engage with the therapy delivery element 24. The engagement of the upper and lower portions 50 limits the amount of compression transferred from the suture material 42 to the anchor sleeve 30, irrespective of the force applied on the distal ends 62 of the suture material 42.

The compression member 40 is preferably generally concentric with the therapy delivery element 24 when in the compressed configuration 66. Consequently, the compression members 40 distributes the force 46 fairly evenly over a greater surface area of the anchor sleeve 30, than conventional anchors.

Figure 5:
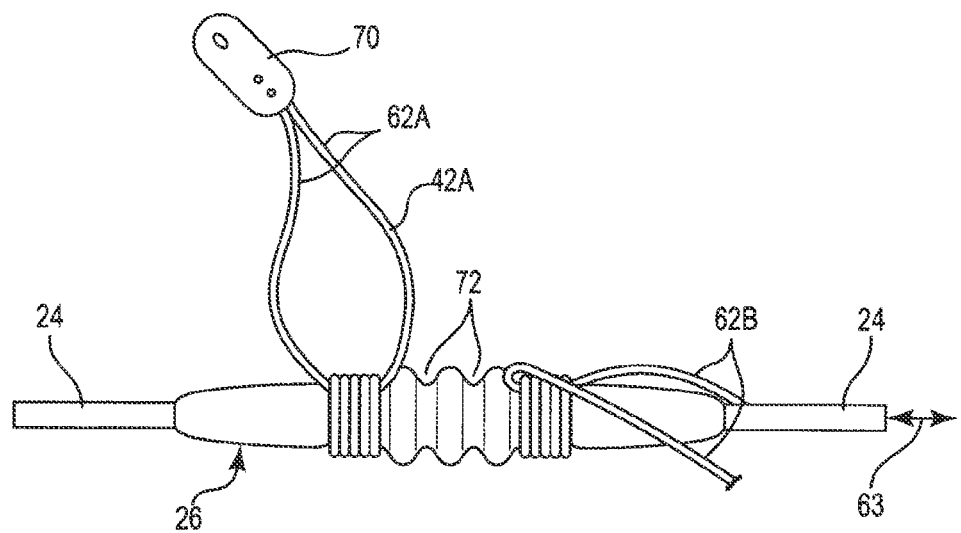
FIG. 5 is a perspective view of the pre-sutured anchor of FIG. 2 engaged with a therapy delivery element in accordance with an embodiment of the present disclosure.

FIG. 5 is a side view of the pre-sutured anchor 26 engaged with the therapy delivery element 24 in accordance with an embodiment of the present disclosure. Plastic cap 70 protects distal ends 62A of the suture material 42A before tensioning. Suture material 42B has already been tensioned and the distal ends 62B are ready to be cut.

Suture grooves 72 formed in the anchor sleeve 30 are provided for receiving suture material 29 used to secure the pre-sutured anchor 26 to the patient 22 (see FIG. 1). Alternatively, distal ends 62 of the suture material 42 can be used to secure the pre-sutured anchor 26 to the patient 22. Once the distal ends 62 are tensioned, the resulting radial compressive force provides sufficient friction to resist longitudinal displacement 63 of the therapy delivery element 24 relative to the anchor sleeve 30.

Figure 6:
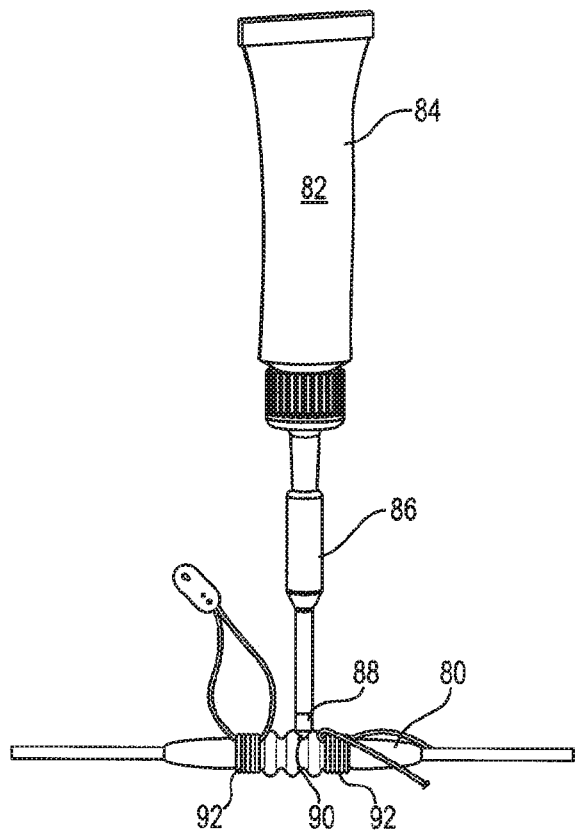
FIG. 6 is a side view of an alternate pre-sutured anchor with a fill port for medical adhesives in accordance with an embodiment of the present disclosure.

FIG. 6 illustrates anchor 80 infused with medical adhesive 82 in accordance with an embodiment of the present disclosure. The medical adhesive 82 is preferably delivered after the anchor 80 is positioned in the desired location along the therapy delivery element 24. The medical adhesive 82 is located in dispenser 84. Dispenser 84 includes adaptor 86 with coupling 88 configured to engage with fill port 90 on anchor sleeve 92. In one embodiment, the coupling 88 and the fill ports 90 include complimentary threats. Because the medical adhesive 82 is applied after the anchor 80 is positioned on the therapy delivery element 24, better bonding results. Moreover, there is no need to slide the anchor 80 into place after the adhesive 82 is applied.

The medical adhesive 82 can be delivered before or after pre-tied knots 92 are tensioned. The medical adhesive 82 can be any type of biocompatible medical-grade adhesive. Such medical adhesive includes polyurethane and/or silicone adhesives. One example is Room Temperature Vulcanization (RTV) silicone adhesive which cures at room temperature. This type of adhesive is generally kept under pressure to prevent it from curing at room temperature. When pressure is removed (e.g., the adhesive is dispensed from the tube) the adhesive will set up, becoming solid, or semi-solid in nature. Another example is a silicone or polyurethane adhesive that cures when exposed to UV or visible light, as is available from the Dymax. Corporation.

Figure 7A:
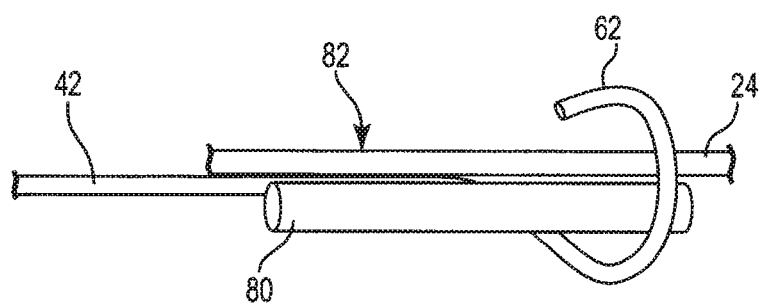
FIG. 7A-7D are schematic illustrations of a method of making an exemplary self-locking compression knot.
Figure 7B:
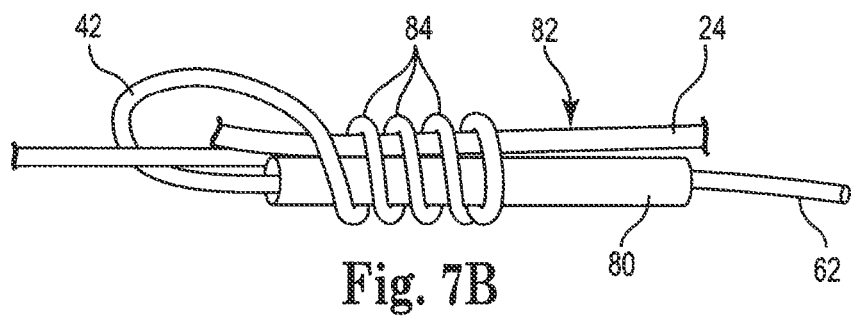

FIGS. 7A through 7D illustrate a method of making nail knot 78 in accordance with an embodiment of the present disclosure. The anchor 24 is shown schematically as a cylindrical rod for the sake of clarity. Hollow tube 100, anchor 24 and a segment of suture material 42 are placed side-by-side in bundle 102. Distal end 62 of the suture material 42 is then looped back onto bundle 102, as illustrated in FIG. 7B. Distal end 62 is then passed through the hollow tube 100. There are typically 4-8 loops 104, although that number will vary with application.

Figure 7C:
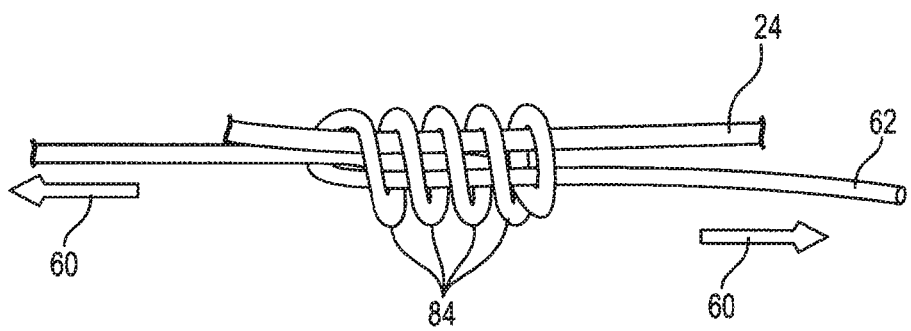
Figure 7D:
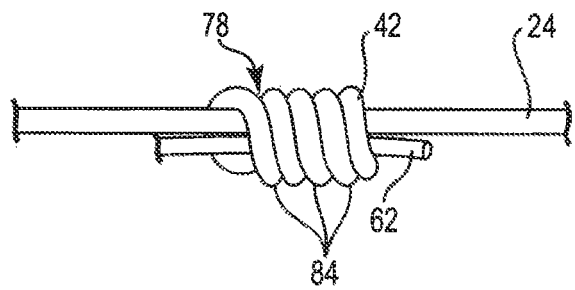

The hollow tube 100 is then slide off of the distal end 62 of the suture material to produce the configuration shown in FIG. 7C. The distal end 62 is located within the loops 104. Opposing tension forces 60 are then applied to the distal ends 62 to cinch the suture material 42 around the pre-sutured anchor 26. The loops 104 preferably to not cross each other.

Figure 8:
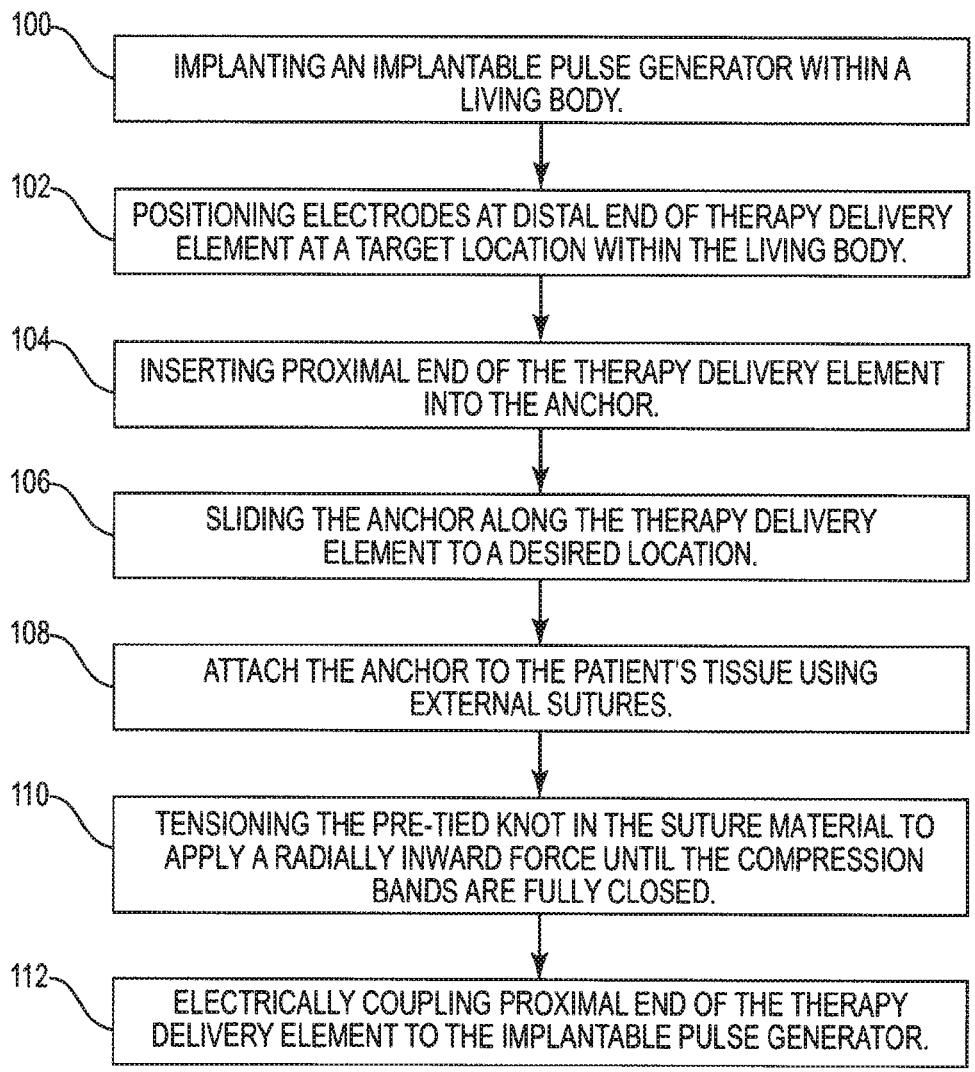
FIG. 8 is a flow diagram of a method of implanting a neurostimulation system within a living body.

FIG. 8 is a flow diagram of a method of implanting a neurostimulation system within a living body. The method includes the steps of implanting an implantable pulse generator within the living body (100). Electrodes at a distal end of a therapy delivery element are positioned at a target location within the living body (102). A proximal end of the therapy delivery element is inserted into lumen in the present anchor (104). The anchor is slide along the therapy delivery element to a desired location (106). The surgeon then sutures the anchor to the patient's tissue, such as for example, using staples or external sutures wrapped around central ribs of the anchor sleeve (108). The surgeon then removes the plastic caps containing the ends of the of the pre-tied suture knots and tightens these knots down until the compression members fully close, preferably by pulling the loose ends of the suture material at the same time (110). Finally, the proximal end of the therapy delivery element is electrically coupled to the implantable pulse generator (112).

With this in mind, a unique aspect of the present anchor is that the surgeon does not have to tie the specific sutures that allow the anchor to grip the lead. Instead, the surgeon only has to pull the ends of the pre-tied knots until the compression members close. The present anchor helps to eliminate the variability that comes from the differing levels of the suturing experience/preference. In terms of using the anchor, the knot's ease of use helps to reduce the amount of time that it takes to engage the anchor. Besides performance, another advantage is that this anchor is cheaper to manufacture than current solutions, like the Medtronic Titan, available from Medtronic, Inc. located in Minneapolis, Minn. or the ANS Cinch Anchor available from St. Jude Medical, Inc. located in St. Paul, Minn. This feature is due to the fact that the present pre-sutured anchor does not have an intricately etched metal insert.

Figure 9A:
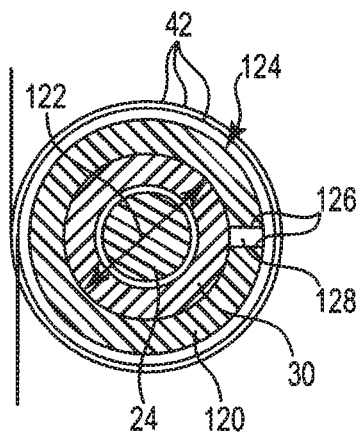
FIG. 9A is a sectional view of an alternate pre-sutured anchor in accordance with an embodiment of the present disclosure.
Figure 9B:
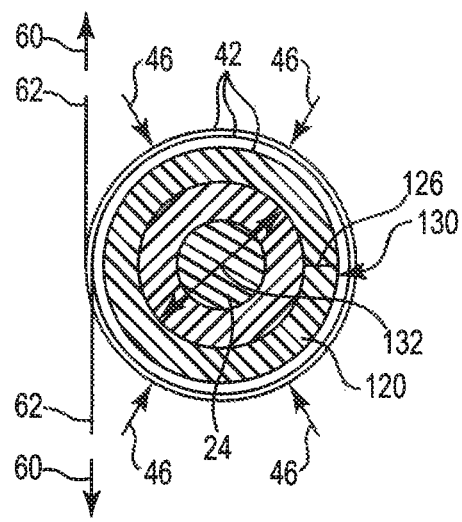
FIG. 9B is a sectional view of the pre-sutured anchor of FIG. 9A in the compressed configuration in accordance with an embodiment of the present disclosure.

FIGS. 9A and 9B are sectional views of an alternate C-shaped compression member 120 in accordance with an embodiment of the present disclosure. As best illustrated in FIG. 9A, the compression member 120 has an inside diameter 122 in open configuration 124 about the same as outside diameter 122 of the compression grooves 38 on the anchor sleeve 30 (See FIG. 2). Stops 126 are separated by compression gaps 128 in the open configuration 124.

As best illustrated in FIG. 9B, tension force 60 is applied to distal ends 62 of the suture material 42, which generates radial compression force 46 that is applied to the compression member 120. The compression member 120 is displaced radially inward by the force 46 until stops 126 engage in compressed configuration 130. The compression member 120 can be deformed elastically or plastically. The compression member 120 has an inside diameter 132 in the compressed configuration 130 that is less than outside diameter 122 of the anchor sleeve 30. The force 46 is sufficient to elastically deform the anchor sleeve 30 a sufficient amount to frictionally engage with the therapy delivery element 24.

FIG. 10 illustrates an alternate pre-sutured anchor 26B substantially as shown in FIG. 2, except that the compression members 40 are removed. The suture material 42 is preferably configured to distribute the compression force 46 so as to not puncture the anchor sleeve 30.

Figure 11A:
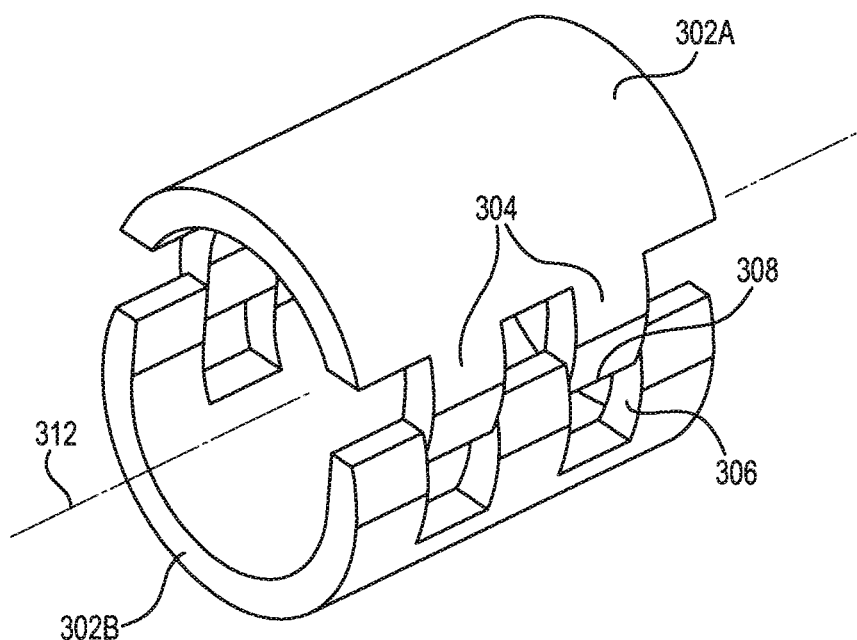
FIGS. 11A and 11B are a perspective view of an alternate compression member in accordance with an embodiment of the present disclosure.
Figure 11B:
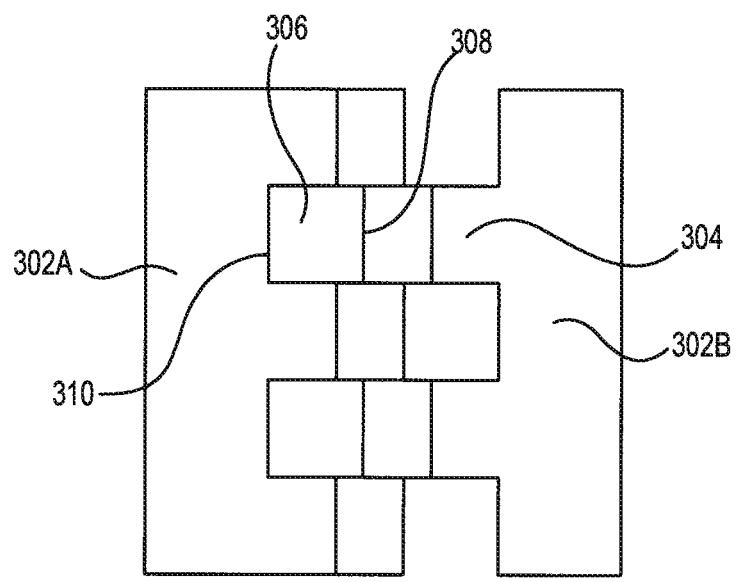

FIGS. 11A and 11B illustrate an alternate compression member 300 for use in a pre-sutured anchor in accordance with an embodiment of the present disclosure. The compression member 300 includes two or more portion 302A, 302B. The portion 302A includes a plurality of protrusions 304 that engage with corresponding recesses 306 on portion 302B. Distal ends 308 of the protrusions 304 and bottom surfaces 310 of the recesses 306 act as stops to limit the compression applied to a therapy delivery element (see e.g., FIG. 4B). The interlaced features 304, 306 also reduce translation of the portions 302 along axis 312.

Figure 12A:
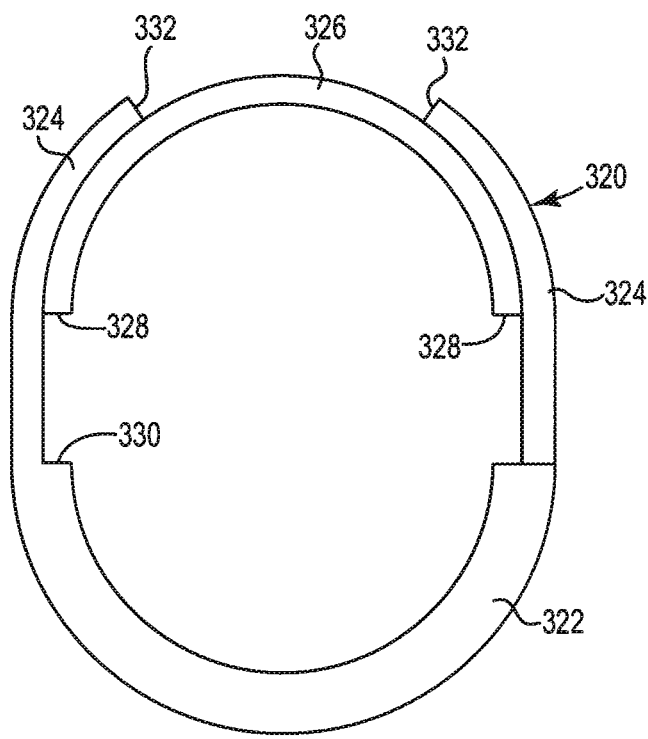
FIGS. 12A and 12B are a perspective view of an alternate compression member in accordance with an embodiment of the present disclosure.
Figure 12B:
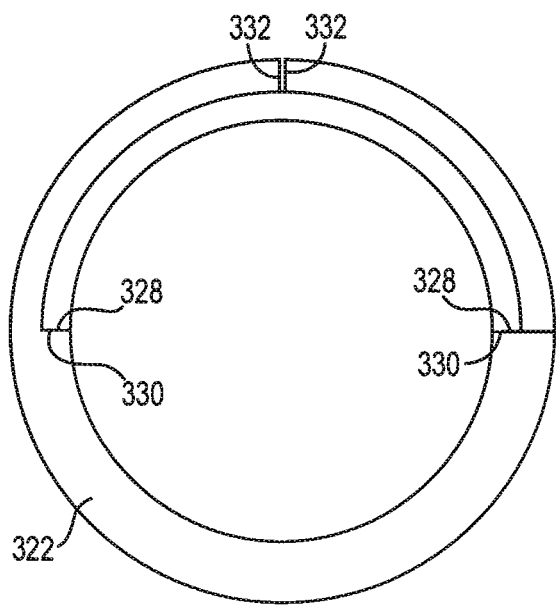

FIGS. 12A and 12B illustrate an alternate compression member 320 for use in a pre-sutured anchor in accordance with an embodiment of the present disclosure. Portion 322 includes extension 324 that wrap around and engage with portion 326. As best illustrated in FIG. 12B, distal ends 328 of portion 326 and edges 330 on portion 322 are primary stops that limit compression applied to a therapy delivery element. Engagement of distal ends 332 of the extension 324 optionally act as secondary stops.

Where a range of values is provided, it is understood that each intervening value, to the tenth of the unit of the lower limit unless the context clearly dictates otherwise, between the upper and lower limit of that range and any other stated or intervening value in that stated range is encompassed within this disclosure. The upper and lower limits of these smaller ranges which may independently be included in the smaller ranges is also encompassed within the disclosure, subject to any specifically excluded limit in the stated range. Where the stated range includes one or both of the limits, ranges excluding either both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the various methods and materials are now described. All patents and publications mentioned herein, including those cited in the Background of the application, are hereby incorporated by reference to disclose and described the methods and/or materials in connection with which the publications are cited.

The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates which may need to be independently confirmed.

Other embodiments are possible. Although the description above contains much specificity, these should not be construed as limiting the scope of the disclosure, but as merely providing illustrations of some of the presently preferred embodiments. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form varying modes disclosed. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

What is claimed is:

1. An anchor configured to secure a therapy delivery element to a desired location of a living body, the anchor comprising:
   an anchor sleeve including:
      a lumen configured to receive the therapy delivery element; and
      an outer surface with a compression groove oriented generally co-axially with respect to the lumen; and
   a suture material pre-tied in a self-locking compression knot extending around the compression groove, wherein, with application of a tension force to at least an end of the suture material, the suture material applies a radial compression force to compress the compression groove and compressively engage the therapy delivery element within the anchor sleeve.

2. The anchor of claim 1, comprising a compression member disposed within the compression groove, the compression member including:
   an open configuration wherein the lumen of the anchor sleeve is unconstricted by the compression member; and
   a compressed configuration wherein the lumen of the anchor sleeve is constricted by the compression member.

3. The anchor of claim 2, wherein the compression member, in the closed configuration, deforms the anchor sleeve.

4. The anchor of claim 2, wherein the compression member includes at least one C-shaped structure.

5. The anchor of claim 2, wherein the compression member includes a gap in the open configuration, the gap being at least partially closed in the compressed configuration of the compression member.

6. The anchor of claim 2, wherein the compression member is configured to plastically deform in response to the radial compression force.

7. The anchor of claim 2, wherein the self-locking compression knot includes at least three loops disposed around the compression member.

8. The anchor of claim 1, wherein the self-locking compression knot includes a nail knot.

9. The anchor of claim 1, comprising a break-away tab attached to the end of the suture material, the break-away tab limiting the tension force applied to the suture material.

10. An anchor configured to secure a therapy delivery element to a desired location of a living body, the anchor comprising:
    an anchor sleeve including:
       a lumen configured to receive the therapy delivery element; and
       an outer surface with a compression groove oriented generally co-axially with respect to the lumen;
    a compression member disposed within the compression groove, the compression member including:
       an open configuration wherein the lumen of the anchor sleeve is unconstricted by the compression member; and
       a compressed configuration wherein the lumen of the anchor sleeve is constricted by the compression member; and
    a suture material pre-tied in a self-locking compression knot extending around the compression groove, wherein, with application of a tension force to at least an end of the suture material, the suture material applies a radial compression force to place the compression member into the compressed configuration to compressively engage the therapy delivery element within the anchor sleeve.

11. The anchor of claim 10, wherein the compression member includes at least one C-shaped structure.

12. The anchor of claim 11, wherein the compression member includes a gap in the open configuration, the gap being at least partially closed in the compressed configuration of the compression member.

13. The anchor of claim 11, wherein the compression member includes at least two C-shaped structures disposed within the compression groove, the at least two C-shaped structures forming a substantially annular shape.

14. The anchor of claim 13, wherein the at least two C-shaped structures are separated by at least one gap in the open configuration, the gap being at least partially closed in the compressed configuration of the compression member.

15. The anchor of claim 10, wherein the compression member is configured to plastically deform in response to the radial compression force.

16. The anchor of claim 10, comprising a break-away tab attached to the end of the suture material, the break-away tab limiting the tension force applied to the suture material.

17. A neurostimulation system comprising:
    an implantable pulse generator;
    a therapy delivery element including:
       a proximal end including a contact configured to electrically couple with the implantable pulse generator; and
       a distal end including an electrode electrically coupled to the contact of the proximal end;
    an anchor configured to secure the therapy delivery element to a desired location of a living body, the anchor including:
       an anchor sleeve including:
          a lumen configured to receive the therapy delivery element; and
          an outer surface with a compression groove oriented generally co-axially with respect to the lumen; and
       a suture material pre-tied in a self-locking compression knot extending around the compression groove, wherein, with application of a tension force to at least an end of the suture material, the suture material applies a radial compression force to compress the compression groove and compressively engage the therapy delivery element within the anchor sleeve.

18. The neurostimulation system of claim 17, wherein the anchor includes a compression member disposed within the compression groove, the compression member including:
   an open configuration wherein the lumen of the anchor sleeve is unconstricted by the compression member; and
   a compressed configuration wherein the lumen of the anchor sleeve is constricted by the compression member.

19. The neurostimulation system of claim 18, wherein the compression member includes at least one C-shaped structure.

20. The neurostimulation system of claim 18, wherein the compression member includes a gap in the open configuration, the gap being at least partially closed in the compressed configuration of the compression member.

* * * * *